United States Patent [19]
Luderer et al.

[11] Patent Number: 5,692,519
[45] Date of Patent: Dec. 2, 1997

[54] METHODS FOR DETERMINING SUITABLE PATIENTS FOR PROSTATE SURGERY INCORPORATING A PROSTATE NEEDLE BIOPSY

[75] Inventors: Albert A. Luderer, Weston; William E. McDowell, Oxford, both of Conn.

[73] Assignee: Dianon Systems, Inc, Stratford, Conn.

[21] Appl. No.: 393,213

[22] Filed: Feb. 23, 1995

[51] Int. Cl.⁶ .................................................. A61B 10/00
[52] U.S. Cl. ........................................................ 128/754
[58] Field of Search ............................ 128/749, 751–754, 128/771; 606/116; 378/162–165; 604/317

[56] References Cited

U.S. PATENT DOCUMENTS

| | | | |
|---|---|---|---|
| 4,600,014 | 7/1986 | Beraha | 128/754 |
| 5,052,035 | 9/1991 | Krupnick | 376/162 |
| 5,122,147 | 6/1992 | Sewell | 606/116 |
| 5,195,533 | 3/1993 | Chin et al. | 128/754 |
| 5,383,472 | 1/1995 | Devlin et al. | 378/164 |

OTHER PUBLICATIONS

Hodge et al. "Random Systematic . . . The Prostate" The Jnl of Urology vol. 142 Jul. 1989.

*Primary Examiner*—Max Hindenburg
*Attorney, Agent, or Firm*—Brian D. Voyce

[57] ABSTRACT

The present invention relates to novel methods for determining whether a patient is suitable for prostate surgery, including novel pathology reports and tissue samples. If a patient has a suspicious prostate, a needle biopsy is performed that enables one to map where a tissue anomaly lies with respect to a prostate sextant location, and how far it lies from the prostate capsule. The present method enables a physician to determine if a patient is suitable for prostate surgery, i.e., has at least one malignant tissue anomaly that has not penetrated or is not about to penetrate the prostate capsule. In a preferred form, the present method can enable the physician to determine if a nerve-sparing prostate surgery can be performed on a patient.

11 Claims, 5 Drawing Sheets

METHODS FOR DETERMINING SUITABLE PATIENTS FOR PROSTATE SURGERY INCORPORATING A PROSTATE NEEDLE BIOPSY

TECHNICAL FIELD

The present invention relates to novel methods for determining whether a patient is suitable for prostate surgery, including novel pathology reports and tissue samples. If a patient has a suspicious prostate, a needle biopsy is performed that enables one to map where a tissue anomaly lies with respect to a prostate sextant location, and how far it lies from the prostate capsule. The present method enables a physician to determine if a patient is suitable for prostate surgery, i.e., has at least one malignant tissue anomaly that has not penetrated or is not about to penetrate the prostate capsule. In a preferred form, the present method can enable the physician to determine if a nerve-sparing prostate surgery can be performed on a patient.

BACKGROUND ART

One of the most difficult calls a urologist has to make is whether and how much of the prostate should be removed from a patient who has prostate cancer. Such decisions are not infrequent in that prostate cancer is currently the second leading cause of cancer death in men, over 200,000 new cases and 38,000 deaths in 1994 alone. The most common means of detecting prostate cancer is with the combination of a digital rectal examination (DRE) and an immunoassay for prostate specific antigen (PSA). Besides DRE, transrectal ultrasound (TRUS) has also become established as a diagnosis tool. A relatively new method involves taking needle biopsies of the prostate transrectally, using ultrasound to guide the physician. (Lee, F. et al., 1987, *Radiology*, 7:627–637).

The concept of performing a sextant biopsy of the prostate was established by Hodges in 1989. A sextant biopsy comprises taking six samples from a prostate, three from each lobe. (See Hodge, K. K. et al., 1989, *J. Urol.*, 142:66–70). By taking a series of samples, one can detect tissue anomalies in different portions of the prostate.

SUMMARY OF THE INVENTION

The present invention relates to novel methods for determining whether a patient is suitable for prostate surgery, including novel pathology reports and tissue samples. A patient is identified as having a suspicious prostate by conventional techniques such as DRE or TRUS. If a suspicious prostate is detected, then a needle biopsy is performed that enables one to map where a tissue anomaly lies with respect to a prostate sextant location, and how far it lies from the prostate capsule.

The needle biopsy comprises obtaining six tissue samples, one each from the left base, the left mid-section, the left apex, the right base, the right mid-section, and the right apex of the prostate of the patient. A conventional biopsy needle is used. The tissue sample should be long enough, i.e., penetrate deep enough, to determine that cancerous material has not penetrated the prostatic capsule. Typically a tissue sample ranges from 3 mm to 17 mm. Each tissue sample is visually inspected for tissue anomalies. The tissue anomalies in the prostate are mapped by recording a pathological description of each tissue anomaly in each tissue sample and identifying the distance each tissue anomaly is from the prostate capsule. The results of a pathological analysis of all tissue samples can be incorporated into a diagrammatic report.

The extent of prostate cancer in the patient by analyzing the presence, the nature, and the size of tissue anomalies. If no anomalies are found, then the patient does not have prostate cancer, and no surgery is needed. If anomalies are found and the cancer has penetrated the prostatic capsule, then the patient has cancer, but the disease is too far developed to warrant the invasive surgery. If anomalies are found but they have not penetrated the prostatic capsule, then the patient is suitable for surgery. The present method also enables one to differentiate between candidates for nerve sparing prostate surgery, as opposed to radical prostate surgery. With the present method, the physician can be presented with organized, immediate reports that greatly enable such decision-making.

PREFERRED EMBODIMENTS

Needle Biopsy Technique

Figure 1:
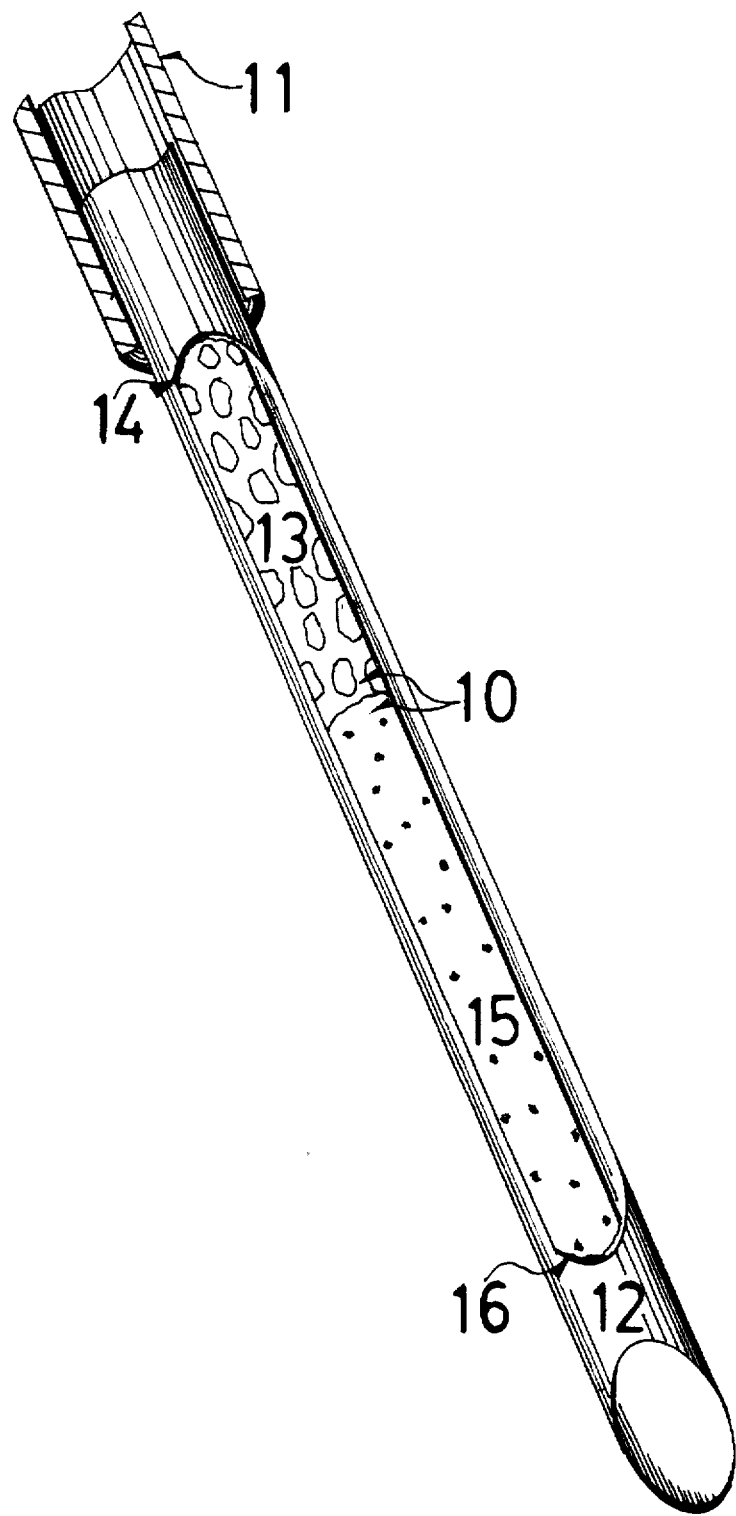
FIG. 1 is a sectional view of the cutting tip of a biopsy needle containing a tissue sample.

An important part of the present method for determining suitable patients for prostate surgery is recording the location and distance of a tissue anomaly from the edge of the tissue sampled. In order to do so in a consistent and verifiable manner, the needle biopsy should be done in a specific manner. The preferred method for identifying the spatial orientation of tissue samples from a needle biopsy comprises obtaining a tissue sample (10) from a predetermined sampling area using a biopsy needle (12) and removing the sample from the needle such that the distal end (14) and the proximal end (16) of the sample are oriented in a predetermined position, as shown in FIG. 1. The tissue sample shown in FIG. 1 shows a section of prostate tissue having normal cells (15) as well as a section having abnormal cancerous cells (13). This can be done using ultrasound-guided biopsy guns. Either the distal end or the proximal end of the tissue sample is marked by applying a color marking (18) means visible under visible, infrared, or ultraviolet light. For the purposes of the present invention, the "proximal" end of a sample from a needle biopsy refers to the portion of the core within the needle bore that is furthest from the tip of the needle, concomitantly, the "distal" end is that closest to the needle tip.) A suitable needle includes a non-pyrogenic, 18 gauge needle having a 20 cm length and a sampling notch of 17 mm, such as a Bard Biopty-Cut$^R$ biopsy needle for use in a Biopty$^R$ instrument made by C. R. Bard, Inc. of Covington, Ga. Still others are known to those of ordinary skill in the art.

Upon the removal of the tissue sample from the biopsy needle, either the distal end or the proximal end of the tissue sample is marked with a coloring or marking agent. Each tissue sample is removed from the needle such that the distal end and the proximal end of the sample are oriented in a predetermined position. Each tissue sample is marked on the distal end or the proximal end by applying a colored marking means visible under visible, infrared, or ultraviolet light, thereby preserving the spatial orientation of each tissue sample. Suitable materials include India ink or other commercially available permanent markers that remain on the surface of the tissue. Preferably, one can use different colors for each of the six tissue samples, identifying the differing sextant locations.

Pathology Report

The combination of sextant prostate biopsy and consistently marked needle biopsy samples provides a powerful tool for the physician. By consistent marking, the pathology results on tissue samples from a needle biopsy can be reported identifying the distance of a tissue anomaly from the edge of the tissue mass sampled with confidence. If the visual pathological inspection reveals a tissue anomaly, then it can be mapped with respect to the location of the predetermined sampling area for each tissue sample and the location of the anomalies with respect to the distal end or the proximal end of each tissue sample.

Figure 2:
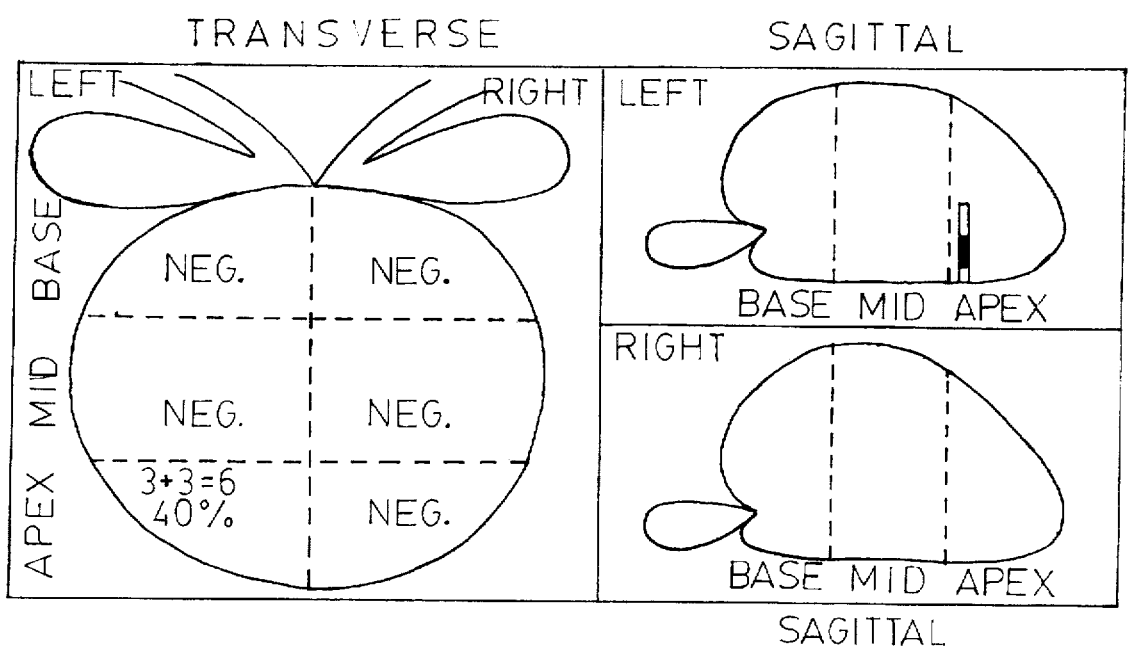
FIG. 2 is a view of a pathology report according to the present invention for a patient with prostate cancer where no surgery is indicated.
Figure 3:
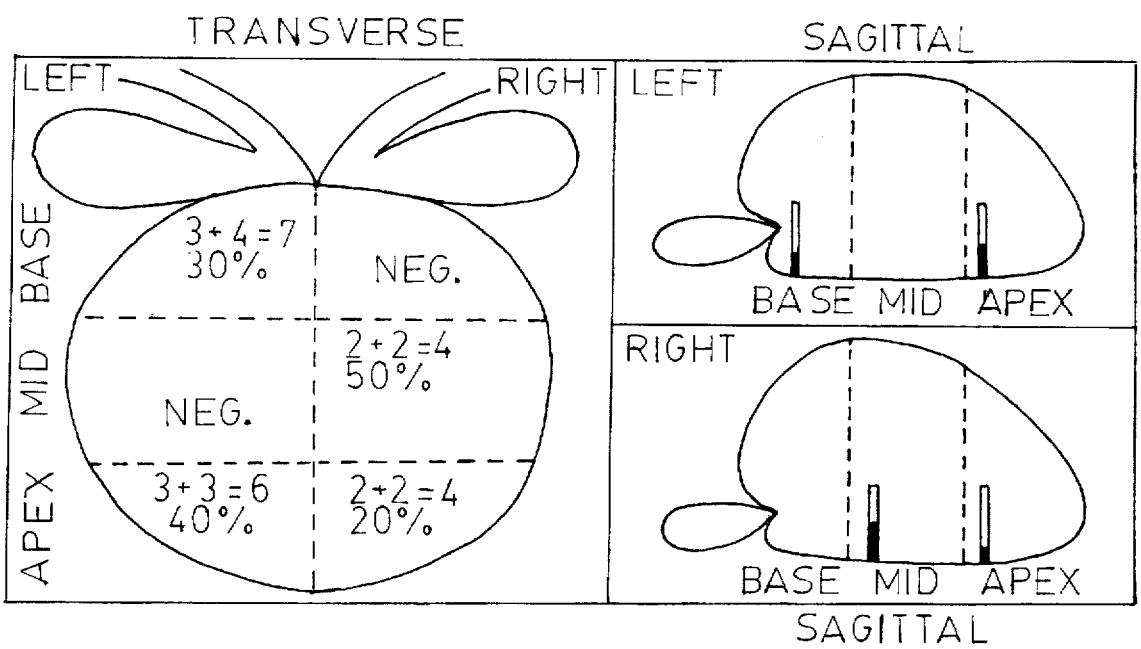
FIG. 3 is a view of a pathology report according to the present invention for a patient with prostate cancer where radical surgery is indicated.
Figure 4:
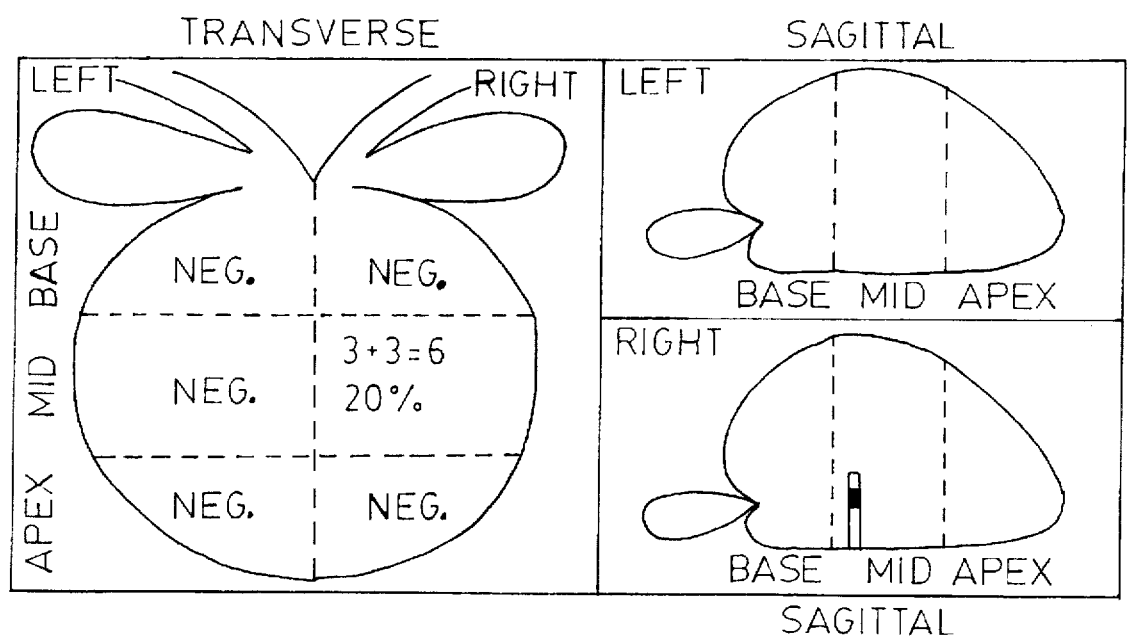
FIG. 4 is a view of a pathology report according to the present invention for a patient with prostate cancer where nerve-sparing prostate surgery is indicated.
Figure 5:
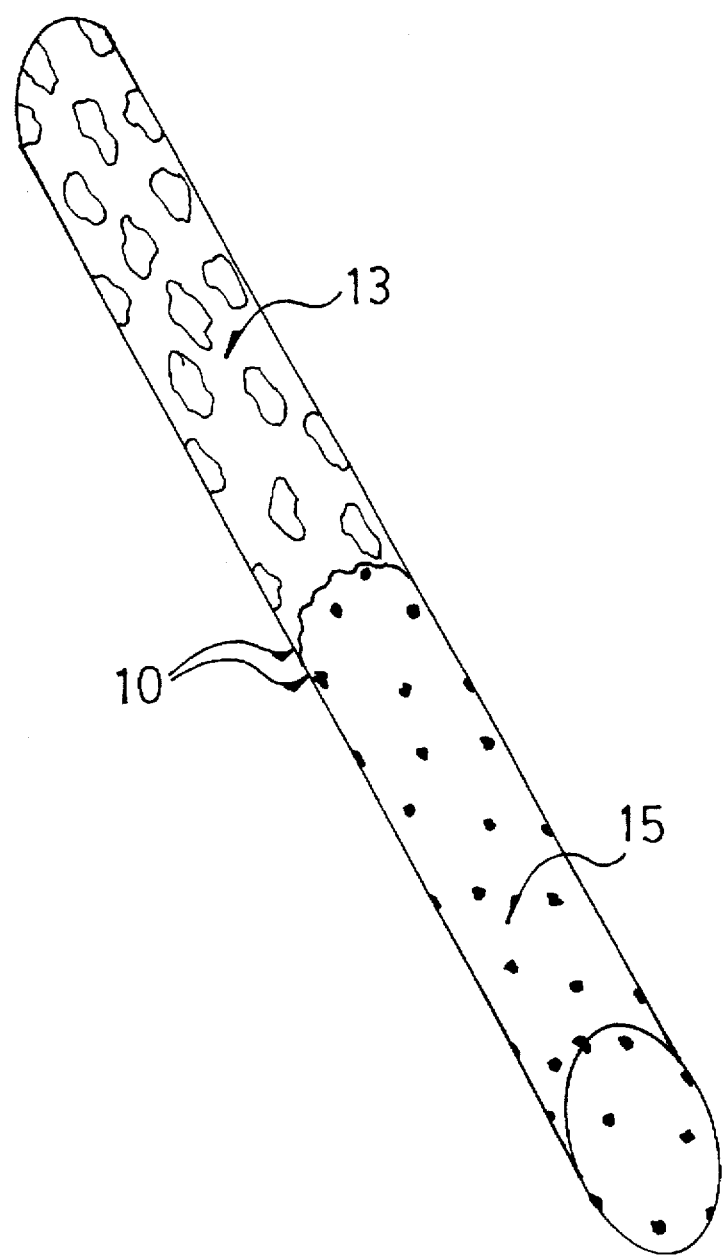
FIG. 5 is a view of a needle biopsy tissue sample removed from the biopsy needle.

Examples of such pathology reports used for a prostate needle biopsy are illustrated in FIGS. 2 to 4. The report (20) comprises a schematic sextant map (22) having six areas corresponding to the marked tissue samples obtained from the left base, the left mid-section, the left apex, the right base, the right mid-section, and the right apex of the prostate. Also included can be a left sagittal or sectional view of the prostate (24) and a right sagittal view (26) showing the angles and the locations at which, and the depths to which the needle was inserted. Any tissue anomalies revealed by visual inspection are recorded, specifically noting in the sextant map and the sagittal views where each tissue sample came from in the prostate and the distance each tissue anomaly is from the prostate capsule. Typically, one would mark the proximal end of the tissue sample, that portion which is closest to the prostatic capsule.

Micrometastasis Testing

Another preferred additional step in the present method is to test the patient for micrometastasis, the spreading of prostate cancer beyond the prostate capsuled. A blood sample is obtained from the patient. The blood sample is assayed for micrometastasis by determining the amount of prostate specific antigen (PSA) positive cells in circulation using a reverse transcriptase—polymerase chain reaction assay specific for prostate specific antigen messenger RNA. Such assays are known to those of ordinary skill in the art and are available to the physician on an investigational basis. These tests are extremely sensitive at detecting PSA positive cells in the general circulation. If micrometastasis is detected, then the physician would not be inclined to perform any kind of prostate surgery, it essentially being too late for such treatment. (See Katz A. E., et al., 1994, Urol., 43: 765–775.)

Nerve-Sparing Prostate Surgery

Probably the most useful aspect of the present method is that it affords the urologist the ability to make more cogent decisions regarding which patients are suitable for nerve-sparing prostate surgery. Two of the terrible side effects of a radical prostatectomy are impotence and incontinence. In large part these are due to the fact that the neurovascular bundles present on the left apex and right apex of the prostate are removed. Nerve-sparing prostate surgery is available; one simply leaves the portions of the apex incorporating or adjacent to the neurovascular bundles. However, in the past, such a decision carried with it the considerable risk that the surgeon was leaving malignant tissue in the patient. Over time, the cancer would spread and become metastatic, rendering the nerve-sparing surgery useless. By knowing not only whether malignant tissue anomalies are present in the apex, but how close such tissue is to the neurovascular bundles and the prostate capsule, the physician can make a reasoned decision, along with the patient, as to whether the neurovascular bundle can be spared and the malignancies removed.

Antibody Staining

If a visual inspection of a tissue sample by a pathologist reveals an indeterminate tissue condition, then additional testing of the tissue is preferred. (As known to those of ordinary skill in the art, "indeterminate tissue condition" refers to an observation of a tissue that reveals tissue abnormalities but not conclusive malignant structure.) In particular, one can perform tissue staining or marking to eliminate non-malignant conditions. For example, a color-labelled antibody specific to cytokeratin, such as CK-903 available from Enzo Biochemicals of New York, N.Y., can be applied to the tissue sample so as to reveal if the indeterminate tissue condition is a non-cancerous lesion. Techniques for visualizing cytokeratin techniques are known to those of ordinary skill in the art of immunohistochemistry. (See Hedrick L. and Epstein, J. I., 1989, Amer. J. of Surg. Path., 13: 389–396.)

EXAMPLES

FIG. 2 illustrates a pathology report for a patient that has prostate cancer but is not a candidate for prostate surgery. The transverse view shows that the left base, the left apex, the right mid-section, and the right apex all have cancerous material. (The numbers in the formulas shown are Gleason numbers conventionally used in pathology reporting.) The sagittal views show that, in all samples, the cancer is located at and penetrates the prostatic capsule. (The dark portions of the bars represent malignant cancerous material.)

FIG. 3 illustrates a pathology report for a patient that has prostate cancer and is a candidate for radical prostate surgery. The transverse view shows that only the left apex has cancerous material. (The numbers in the formulas shown are Gleason numbers conventionally used in pathology reporting.) The sagittal views show that the cancer does not penetrate the prostatic capsule. (The dark portions of the bars represent malignant cancerous material, which does not touch the outside line of the view.)

FIG. 4 illustrates a pathology report for a patient that has prostate cancer and is a candidate for nerve-sparing prostate surgery. The transverse view shows that only the right mid-section has cancerous material. (The numbers in the formulas shown are Gleason numbers conventionally used in pathology reporting.) The sagittal views show that the cancer is located at and does not penetrate the prostatic capsule. Equally important, the cancer does not approach the prostate apex, and thus, the nerve bundle near the apex does not have to be removed. (The dark portions of the bars represent malignant cancerous material.)

All publications or unpublished patent applications mentioned herein are hereby incorporated by reference thereto.

Other embodiments of the present invention are not presented here which are obvious to those of skill in the art, now or during the term of any patent issuing herefrom, and thus, are within the spirit and scope of the present invention.

We claim:

1. A method for determining whether a patient is suitable for prostate surgery comprising:
   a) obtaining a tissue sample, respectively, from the left base, the left mid-section, the left apex, the right base, the right mid-section, and the right apex of the prostate of the patient by means of a needle biopsy;
   b) visually inspecting each tissue sample for tissue anomalies;
   c) mapping the tissue anomalies in the prostate by recording a pathological description of each tissue anomaly in each tissue sample and the distance each tissue anomaly is from the prostate capsule; and d) deciding the extent of prostate cancer in the patient by analyzing the presence, the nature, and the size of tissue anomalies, a suitable patient comprising one having at least one malignant tissue anomaly that has not penetrated or is not about to penetrate the prostate capsule.

2. The method of claim 1 for determining whether a patient is suitable for prostate surgery wherein each tissue sample is removed from the needle such that the distal end and the proximal end of the sample are oriented in a predetermined position, and each tissue sample is marked on the distal end or the proximal end by applying a colored marking means visible under visible, infrared, or ultraviolet light, thereby preserving the spatial orientation of each tissue sample.

3. The method of claim 1 for determining whether a patient is suitable for prostate surgery wherein if the visual inspection of a tissue sample reveals an indeterminate tissue condition, a color-labelled antibody specific to cytokeratin is applied to the tissue sample so as to reveal if the indeterminate tissue condition is a non-cancerous lesion.

4. The method of claim 1 for determining whether a patient is suitable for prostate surgery also comprising:

a) obtaining a blood sample from the patient;

b) assaying the blood sample for micrometastasis by determining the amount of prostate specific antigen positive cells in circulation using a reverse transcriptase—polymerase chain reaction assay specific for prostate specific antigen; and c) deciding the extent of prostate cancer in the patient by analyzing the presence, the nature, and the size of tissue anomalies and the presence of micrometastasis, a suitable patient comprising one having at least one malignant tissue anomaly that has not penetrated or is not about to penetrate the prostate capsule, and does not have micrometastasis.

5. A method for determining whether a patient is suitable for nerve-sparing prostate surgery comprising:

a) obtaining a tissue sample, respectively, from the left base, the left mid-section, the left apex, the right base, the right mid-section, and the right apex of the prostate of the patient by means of a needle biopsy;

b) visually inspecting each tissue sample for tissue anomalies;

c) mapping the tissue anomalies in the prostate by recording a pathological description of each tissue anomaly in each tissue sample and the distance each tissue anomaly is from the prostate capsule; and d) deciding the extent of prostate cancer in the patient by analyzing the presence, the nature, and the size of tissue anomalies, a suitable patient comprising one having at least one malignant tissue anomaly that has not penetrated or is not about to penetrate the prostate capsule and does not have a malignant tissue anomaly close to the neurovascular bundles in either the left apex or the right apex of the prostate.

6. The method of claim 5 for determining whether a patient is suitable for nerve-sparing prostate surgery wherein each tissue sample is removed from the needle such that the distal end and the proximal end of the sample are oriented in a predetermined position, and each tissue sample is marked on the distal end or the proximal end by applying a colored marking means visible under visible, infrared, or ultraviolet light, thereby preserving the spatial orientation of each tissue sample.

7. The method of claim 5 for determining whether a patient is suitable for nerve-sparing prostate surgery wherein if the visual inspection of a tissue sample reveals an indeterminate tissue condition, a color-labelled antibody specific to cytokeratin is applied to the tissue sample so as to reveal if the indeterminate tissue condition is a non-cancerous lesion.

8. The method of claim 5 for determining whether a patient is suitable for nerve-sparing prostate surgery also comprising:

a) obtaining a blood sample from the patient;

b) assaying the blood sample for micrometastasis by determining the amount of prostate specific antigen positive cells in circulation using a reverse transcriptase—polymerase chain reaction assay specific for prostate specific antigen; and c) deciding the extent of prostate cancer in the patient by analyzing the presence, the nature, and the size of tissue anomalies and the presence of micrometastasis, a suitable patient comprising one having at least one malignant tissue anomaly that has not penetrated or is not about to penetrate the prostate capsule, does not have micrometastasis, and does not have a malignant tissue anomaly close to the neurovascular bundles in either the left apex or the right apex of the prostate.

9. A method for identifying the spatial orientation of tissue samples from a needle biopsy comprising:

a) obtaining a tissue sample from a predetermined sampling area using a biopsy needle;

b) removing the sample from the needle such that the distal end and the proximal end of the sample are oriented in a predetermined position; and c) marking the distal end or the proximal end of the tissue sample by applying a color marking means visible under visible, infrared, or ultraviolet light.

10. A method for reporting pathology results on tissue samples from a needle biopsy comprising:

a) obtaining at least one tissue sample, each from a predetermined sampling area using a biopsy needle;

b) removing each sample from the needle such that the distal end and the proximal end of the sample are oriented in a predetermined position;

c) marking the distal end or the proximal end of each tissue sample by applying a color marking means visible under visible, infrared, or ultraviolet light;

d) visually inspecting each tissue sample for any tissue anomalies; and e) mapping the tissue anomalies in each tissue sample with respect to the location of the predetermined sampling area for each tissue sample and the location of the anomalies with respect to the distal end or the proximal end of each tissue sample.

11. The method of claim 10 for reporting pathology results on a series of tissue samples taken from a prostate comprising:

a) obtaining a tissue sample from, respectively, the left base, the left mid-section, the left apex, the right base, the right mid-section, and the right apex of the prostate; and b) recording the distance each tissue anomaly is from the prostate capsule in each tissue sample in mapping the tissue anomalies.

\* \* \* \* \*